(12) United States Patent
Pan et al.

(10) Patent No.: US 7,256,206 B2
(45) Date of Patent: Aug. 14, 2007

(54) BICYCLIC COMPOUNDS AND COMPOSITIONS

(75) Inventors: Shifeng Pan, San Diego, CA (US); Nathanael S. Gray, San Diego, CA (US); Yuan Mi, San Diego, CA (US); Wenqi Gao, San Diego, CA (US); Yi Fan, Poway, CA (US); Sophie Lefebvre, San Diego, CA (US)

(73) Assignee: IRM LLC, Hamilton (BM)

( * ) Notice: Subject to any disclaimer, the term of this patent is extended or adjusted under 35 U.S.C. 154(b) by 439 days.

(21) Appl. No.: 10/776,946

(22) Filed: Feb. 11, 2004

(65) Prior Publication Data
US 2004/0248952 A1 Dec. 9, 2004

Related U.S. Application Data

(60) Provisional application No. 60/446,648, filed on Feb. 11, 2003, provisional application No. 60/464,809, filed on Apr. 21, 2003, provisional application No. 60/472,012, filed on May 19, 2003.

(51) Int. Cl.
*A61K 31/421* (2006.01)
*C07D 263/30* (2006.01)
*C07D 261/06* (2006.01)

(52) U.S. Cl. .............. 514/374; 548/215; 548/235; 548/240; 548/247; 514/378

(58) Field of Classification Search .............. 548/215, 548/235, 240, 247; 514/374, 378
See application file for complete search history.

(56) References Cited

U.S. PATENT DOCUMENTS

2004/0048857 A1 3/2004 Pan et al.

FOREIGN PATENT DOCUMENTS

EP 0 788 263 A1 * 6/1997

* cited by examiner

*Primary Examiner*—Golam M. M. Shameem
(74) *Attorney, Agent, or Firm*—Scott W. Reid; Genomics Institute of the Novartis Research Foundation

(57) ABSTRACT

The present invention relates to bicyclic derivatives, process for their production, their uses and pharmaceutical compositions containing them. The invention provides a novel class of compounds useful in the treatment or prevention of diseases or disorders mediated by lymphocyte interactions, particularly diseases associated with EDG/S1P receptor mediated signal transduction.

5 Claims, No Drawings

BICYCLIC COMPOUNDS AND COMPOSITIONS

CROSS-REFERENCE TO RELATED APPLICATIONS

This application claims the benefit of priority to U.S. Provisional Patent Application Nos. 60/446,648 (filed Feb. 11, 2003), 60/464,809 (filed Apr. 21, 2003) and 60/472,012 May 19, 2003). The full disclosures of these applications are incorporated herein by reference in their entirety and for all purposes.

BACKGROUND OF THE INVENTION

1. Field of the Invention

The invention provides a novel class of bicyclic compounds useful in the treatment or prevention of diseases or disorders mediated by lymphocyte interactions, particularly diseases associated with EDG/S1P receptor mediated signal transduction.

2. Background

EDG receptors belong to a family of closely related, lipid activated G-protein coupled receptors. EDG-1, EDG-3, EDG-5, EDG-6, and EDG-8 (also respectively termed S1P1, S1P3, S1P2, S1P4, and S1P5) are identified as receptors specific for sphingosine-1-phosphate (SIP). EDG2, EDG4, and EDG7 (also termed LPA1, LPA2, and LPA3, respectively) are receptors specific for lysophosphatidic (LPA). Among the SIP receptor isotypes, EDG-1, EDG-3 and EDG-5 are widely expressed in various tissues, whereas the expression of EDG-6 is confined largely to lymphoid tissues and platelets, and that of EDG-8 to the central nervous system. EDG receptors are responsible for signal transduction and are thought to play an important role in cell processes involving cell development, proliferation, maintenance, migration, differentiation, plasticity and apoptosis. Certain EDG receptors are associated with diseases mediated by lymphocyte interactions, for example, in transplantation rejection, autoimmune diseases, inflammatory diseases, infectious diseases and cancer. An alteration in EDG receptor activity contributes to the pathology and/or symptomology of these diseases. Accordingly, molecules that themselves alter the activity of EDG receptors are useful as therapeutic agents in the treatment of such diseases.

SUMMARY OF THE INVENTION

This application relates to compounds of Formula I:

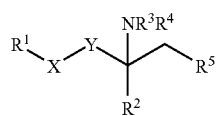

in which:

Y is —CH$_2$CH$_2$—, —CH$_2$CH(OH)—, —CH(OH)CH$_2$—, —C(O)CH$_2$—, —CH$_2$C(O)—, —CH=CH— or 1,2-cyclopropylene;

X is arylene or C$_{5-6}$heteroarylene optionally substituted by one to three substituents selected from halo, C$_{1-10}$alkyl and halo-substituted C$_{1-6}$alkyl;

R$^1$ is a group of formula (a), (b), (c), (d), (e) or (f):

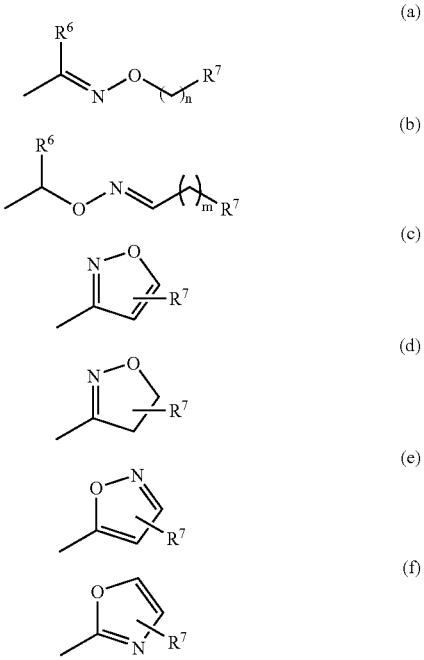

in which:

n is 0, 1, 2, 3, 4 or 5;

m is 0, 1 or 2;

R$^6$ is C$_{1-10}$alkyl, cycloalkyl, C$_{1-10}$alkoxy, C$_{2-10}$alkenyl, C$_{2-10}$alkynyl, C$_{1-10}$alkylthio, C$_{1-10}$alkylsulfonyl, C$_{1-10}$alkylsulfinyl or halo-substituted-C$_{1-10}$alkyl; in each of which any aliphatic part of the group can be straight chain or branched and can be optionally substituted by up to three hydroxy, cycloalkyl, or C$_{1-4}$alkoxy groups and optionally interrupted by a double or triple bond or one or more C(O), NR$^{12}$, S, S(O), S(O)$_2$ or O groups, R$^7$ is aryl or C$_{5-6}$heteroaryl optionally substituted by aryl, C$_{5-6}$heteroaryl or C$_{3-8}$cycloalkyl wherein any aryl, heteroaryl or cycloalkyl group of R$^7$ can be optionally substituted by one to three substituents selected from halogen, C$_{1-10}$alkyl, C$_{1-10}$alkoxy, halo-substituted-C$_{1-10}$alkyl and halo-substituted-C$_{1-10}$alkoxy;

R$^2$ is hydrogen; C$_{1-4}$alkyl optionally substituted with one or more halogens; C$_{2-6}$ alkenyl, C$_{2-6}$alkynyl, or cycloalkyl optionally substituted by halogen; or C$_{1-4}$alkyl optionally substituted on the terminal C atom by OH or a residue of formula (g):

in which Z is O, S, (CH$_2$)$_{1-2}$, CF$_2$ or NR$^{11}$ where R$^{11}$ is H, (C$_{1-4}$)alkyl or halo substituted (C$_{1-4}$)alkyl; and R$^9$ and R$^{10}$, independently, are H, OH, (C$_{1-4}$)alkyl optionally substituted by one to three halo groups, or (C$_{1-4}$)alkoxy; with the proviso that R$^9$ and R$^{10}$ are not both hydrogen;

R$^3$ and R$^4$, independently, are H or C$_{1-4}$alkyl optionally substituted by halogen or acyl; and $R^5$ is —OH, —Oacyl, —NHacyl, or a residue of formula (g) as defined above;

and the N-oxide derivatives, prodrug derivatives, protected derivatives, individual isomers and mixtures of isomers thereof; and the pharmaceutically acceptable salts and solvates (e.g. hydrates) of such compounds.

A second aspect of the invention is a pharmaceutical composition which contains a compound of Formula I or an N-oxide derivative, individual isomer or mixture of isomers thereof, or a pharmaceutically acceptable salt thereof, in admixture with one or more suitable excipients.

A third aspect of the invention is a method for treating a disease in an animal in which alteration of EDG/S1P receptor mediated signal transduction can prevent, inhibit or ameliorate the pathology and/or symptomology of the disease, which method comprises administering to the animal a therapeutically effective amount of a compound of Formula I or a N-oxide derivative, individual isomer or mixture of isomers thereof; or a pharmaceutically acceptable salt thereof.

A fourth aspect of the invention is a method for inhibiting or controlling deregulated angiogenesis, e.g. EDG-1/S1P-1 mediated angiogenesis, in a subject in need thereof, comprising administering to said subject a therapeutically effective amount of a compound of formula I or a pharmaceutically acceptable salt thereof.

A fifth aspect of the invention is a method for preventing or treating diseases mediated by a neo-angiogenesis process or associated with deregulated angiogenesis in a subject in need thereof, comprising administering to said subject a therapeutically effective amount of a compound of formula I or a pharmaceutically acceptable salt thereof.

A sixth aspect of the invention is the use of a compound of Formula I in the manufacture of a medicament for treating a disease in an animal in which alteration of EDG/S1P receptor mediated signal transduction contributes to the pathology and/or symptomology of the disease.

A seventh aspect of the invention is a process for preparing compounds of Formula I and the N-oxide derivatives, prodrug derivatives, protected derivatives, individual isomers and mixtures of isomers thereof; and the pharmaceutically acceptable salts thereof.

DESCRIPTION OF THE PREFERRED EMBODIMENTS

The invention provides compounds that are useful in the treatment and/or prevention of diseases or disorders mediated by lymphocyte interactions. Also provided are methods for treating such diseases or disorders.

Definitions

In this specification, unless otherwise defined:

"Acyl" means a residue R—CO— wherein R is $C_{1-6}$alkyl, $C_{3-6}$cyclopropyl, phenyl or phenyl$C_{1-4}$alkyl.

"Alkyl" as a group and as a structural element of other groups, for example halo-substituted-alkyl, alkoxy, acyl, alkylthio, alkylsulfonyl and alkylsulfinyl, can be either straight-chained or branched. "Alkenyl" as a group and as a structural element of other groups contains one or more carbon—carbon double bonds, and can be either straight-chain, or branched. Any double bonds can be in the cis- or trans-configuration. A preferred alkenyl group is vinyl. "Alkynyl" as a group and as structural element of other groups and compounds contains at least one C≡C triple bond and can also contain one or more C═C double bonds, and can, so far as possible, be either straight-chain or branched. A preferred alkynyl group is propargyl. Any cycloalkyl group, alone or as a structural element of other groups can contain from 3 to 8 carbon atoms, preferably from 3 to 6 carbon atoms.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. For example, arylene as used in this application can be phenylene or naphthylene, preferably phenylene, more preferably 1,4-phenylene.

"Halo" or "halogen" means F, Cl, Br or I, preferably F or Cl. Halo-substituted alkyl groups and compounds can be partially halogenated or perhalogenated, whereby in the case of multiple halogenation, the halogen substituents can be identical or different. A preferred perhalogenated alkyl group is for example trifluoromethyl.

"Heteroaryl" means aryl, as defined in this application, provided that one or more of the ring carbon atoms indicated are replaced by a hetero atom moiety selected from N, O or S, and each ring is comprised of 5 to 6 ring atoms, unless otherwise stated. For example, heteroaryl as used in this application includes thiophenyl, pyridinyl, furanyl, isoxazolyl, benzoxazolyl or benzo[1,3]dioxolyl, preferably thiophenyl, furanyl or pyridinyl. "Heteroarylene" means heteroaryl, as defined in this application, provided that the ring assembly comprises a divalent radical.

As used in the present invention, an EDG-1 selective compound (agent or modulator) has a specificity that is (i) selective for EDG-1 over EDG-3 and over one or more of EDG-5, EDG-6, and EDG-8; or (ii) selective for EDG-1 and EDG-3 over one or more of EDG-5, EDG-6, and EDG-8. As used herein, selectivity for one EDG receptor (a "selective receptor") over another EDG receptor (a "non-selective receptor") means that the compound has a much higher potency in inducing activities mediated by the selective EDG receptor (e.g., EDG-1) than that for the non-selective S1P-specific EDG receptor. If measured in a GTP-γS binding assay (as described in the Example below), an EDG-1 selective compound typically has an EC50 (effective concentration that causes 50% of the maximum response) for a selective receptor (EDG-1, or both EDG-1 and EDG-3 in some embodiments) that is at least 5, 10, 25, 50, 100, 500, or 1000 fold lower than its EC50 for a non-selective receptor (e.g., one or more of EDG-5, EDG-6, and EDG-8).

DETAILED DESCRIPTION OF THE INVENTION

The invention provides compounds that are useful for treating or preventing diseases or disorders that are mediated by lymphocyte interactions. In some embodiments, these compounds are of Formula I:

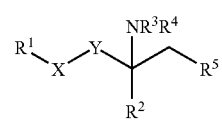

in which:

Y is —CH₂CH₂—, —CH₂CH(OH)—, —CH(OH)CH₂—, —C(O)CH₂—, —CH₂C(O)—, —CH═CH—; or 1,2-cyclopropylene;

X is arylene or $C_{5-6}$heteroarylene optionally substituted by one to three substituents selected from halo, $C_{1-10}$alkyl and halo-substituted $C_{1-6}$alkyl;

$R^1$ is a group of formula (a), (b), (c), (d), (e) or (f):

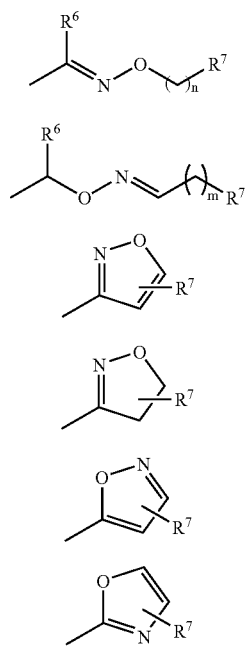

in which n is 0, 1, 2, 3, 4 or 5; m is 0, 1 or 2;

$R^6$ is $C_{1-10}$alkyl, cycloalkyl, $C_{1-10}$alkoxy, $C_{2-10}$alkenyl, $C_{2-10}$alkynyl, $C_{1-10}$alkylthio, $C_{1-10}$alkylsulfonyl, $C_{1-10}$alkylsulfinyl or halo-substituted-$C_{1-10}$alkyl; in each of which any aliphatic part of the group can be straight chain or branched and can be optionally substituted by up to three hydroxy, cycloalkyl, or $C_{1-4}$alkoxy groups and optionally interrupted by a double or triple bond or one or more C(O), $NR^{12}$, S, S(O), S(O)$_2$ or O groups;

$R^7$ is aryl or $C_{5-6}$heteroaryl optionally substituted by aryl, $C_{5-6}$heteroaryl or $C_{3-8}$cycloalkyl wherein any aryl, heteroaryl or cycloalkyl group of $R^7$ can be optionally substituted by one to three substituents selected from halogen, $C_{1-10}$alkyl, $C_{1-10}$alkoxy, halo-substituted-$C_{1-10}$alkyl and halo-substituted-$C_{1-10}$alkoxy;

$R^2$ is hydrogen; $C_{1-4}$alkyl optionally substituted with one or more halogens; $C_{2-6}$ alkenyl, $C_{2-6}$alkynyl, or cycloalkyl optionally substituted by halogen; or $C_{1-4}$alkyl optionally substituted on the terminal C atom by OH or a residue of formula (g):

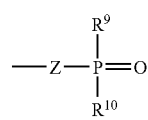

in which Z is O, S, (CH$_2$)$_{1-2}$, CF$_2$ or $NR^{11}$ where $R^{11}$ is H, ($C_{1-4}$)alkyl or halo substituted ($C_{1-4}$)alkyl; and $R^9$ and $R^{10}$, independently, are H, OH, ($C_{1-4}$)alkyl optionally substituted by one to three halo groups, or ($C_{1-4}$)alkoxy; with the proviso that $R^9$ and $R^{10}$ are not both hydrogen;

$R^3$ and $R^4$, independently, are H or $C_{1-4}$alkyl optionally substituted by halogen or acyl; and $R^5$ is —OH, —Oacyl, —NHacyl, or a residue of formula (g) as defined above;

and the N-oxide derivatives, prodrug derivatives, protected derivatives, individual isomers and mixtures of isomers thereof; and the pharmaceutically acceptable salts and solvates (e.g. hydrates) of such compounds.

In one embodiment, for the compounds of Formula I, Y is preferably —CH$_2$—CH$_2$— or —CH(OH)—CH$_2$—, more preferably —CH$_2$—CH$_2$—.

In another embodiment, X is preferably 1,4-phenylene or thiophenylene.

In yet another embodiment, $R^2$ is preferably $R^{2'}$ where $R^{2'}$ is $C_{1-4}$alkyl optionally substituted on the terminal C atom by OH or a residue of formula (g). More preferably $R^2$ is methyl or hydroxymethyl, most preferably hydroxymethyl.

Preferably, at least one of $R^3$ and $R^4$ is hydrogen. More preferably, both are hydrogen.

$R^5$ is preferably $R^{5'}$ in which $R^{5'}$ is H, —OH, —NHC(O) $C_{1-4}$alkyl or a residue of formula (g).

Preferably, in the group of formula (g), each of $R^9$ and $R^{10}$ is —OH.

In a further embodiment, $R^1$ is a group of formula (a), (b) or (d). More preferably, $R^1$ is a group of formula (a).

Preferably, $R^6$ is $C_{1-6}$alkyl, $R^7$ is thiophenyl, furanyl, pyridinyl or phenyl optionally substituted by thiophenyl, furanyl, pyridinyl, phenyl or cyclohexyl wherein any thiophenyl, furanyl, pyridyl, phenyl or cyclohexyl can be optionally substituted by one to three substituents selected from halogen, halo-substituted-$C_{1-10}$alkyl and halo-substituted-$C_{1-10}$alkoxy.

In another embodiment, $R^7$ is phenyl monosubstituted in the para position by thiophenyl, furanyl, pyridyl, phenyl or cyclohexyl.

In another embodiment, n is 3, 4 or 5 and $R^7$ is phenyl. Particularly preferred compounds of Formula I are compounds selected from Table I.

The invention provides forms of the compound that have the hydroxyl or amine group present in a protected form; these function as prodrugs. Prodrugs are compounds that are converted into an active drug form after administration, through one or more chemical or biochemical transformations. Forms of the compounds of the present invention that are readily converted into the claimed compound under physiological conditions are prodrugs of the claimed compounds and are within the scope of the present invention. Examples of prodrugs include forms where a hydroxyl group is acylated to form a relatively labile ester such as an acetate ester, and forms where an amine group is acylated with the carboxylate group of glycine or an L-amino acid such as serine, forming an amide bond that is particularly susceptible to hydrolysis by common metabolic enzymes. Some molecules of the present invention can themselves be prodrugs, such as those comprising a phosphate residue of formula (g) which can be enzymatically dephosphorylated to a hydroxy group. Alternatively, a compound of the invention comprising a free hydroxy group can be enzymatically phosphorylated to a compound comprising a phosphate residue of formula (g). The present invention also includes both the enzymatically phosphorylated or dephosphorylated compounds of Formula I, optionally in equilibrium.

Compounds of Formula I can exist in free form or in salt form, e.g. addition salts with inorganic or organic acids; when group (g) is present and $R^9$ or $R^{10}$ is —OH, group (g) can also be present in salt form, e.g. an ammonium salt or salts with metals such as lithium, sodium, potassium, calcium, zinc or magnesium, or a mixture thereof. Compounds of Formula I and their salts in hydrate or solvate form are also part of the invention.

When the compounds of Formula I have asymmetric centers in the molecule, various optical isomers are obtained. The present invention also encompasses enantiomers, racemates, diastereoisomers and mixtures thereof. For example, the central carbon atom bearing $R^2$, $CH_2—R^5$ and $NR^3R^4$ can have the R or S configuration. Compounds having the R configuration at this central carbon atom are preferred. Moreover, when the compounds of Formula I include geometric isomers, the present invention embraces cis-compounds, trans-compounds and mixtures thereof. Similar considerations apply in relation to starting materials exhibiting asymmetric carbon atoms or unsaturated bonds as mentioned above.

Methods and Pharmaceutical Compositions for Treating Immunomodulatory Conditions The compounds of Formula I in free form or in pharmaceutically acceptable salt form, exhibit valuable pharmacological properties, e.g. lymphocyte recirculation modulating properties, for example, as indicated by the in vitro and in vivo tests of Example 3 and are therefore indicated for therapy. Compounds of Formula I preferably show an $EC_{50}$ in the range of $1 \times 10^{-10}$ to $1 \times 10^{-5}$ M, preferably less than 50 nM. The compounds exhibit selectivity for one or more EDG/S1P receptors, preferably EDG-1/S1P-1. EDG-1/S1P-1 selective modulators of the present invention can be identified by assaying a compound's binding to EDG-1/S1P-1 and one or more of the other EDG/S1P receptors (e.g., EDG-3/S1P-3, EDG-5/S1P-2, EDG-6/S1P-4, and EDG-8/S1P-5). An EDG-1/S1P-1 selective modulator usually has an EC50 for the EDG-1/S1P-1 receptor in the range of $1 \times 10^{-10}$ to $1 \times 10^{-5}$ M, preferably less than 50 nM, more preferably less than 5 nM. It also has an EC50 for one or more of the other EDG/S1P receptors that is at least 5, 10, 25, 50, 100, 500, or 1000 fold higher than its EC50 for EDG-1/S1P-1. Thus, some of the EDG-1/S1P-1 modulatory compounds will have an EC50 for EDG-1/S1P-1 that is less than 5 nM while their EC50 for one or more of the other EDG/S1P receptors are at least 100 nM or higher. Other than assaying binding activity to the EDG/S1P receptors, EDG-1/S1P-1 selective agents can also be identified by examining a test agent's ability to modify a cellular process or activity mediated by an EDG/S1P receptor.

The compounds of formula I are, therefore, useful in the treatment and/or prevention of diseases or disorders mediated by lymphocytes interactions, for example in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

Furthermore, the compounds of formula I are useful in cancer chemotherapy, particularly for cancer chemotherapy of solid tumors, e.g. breast cancer, or as an anti-angiogenic agent.

The required dosage will of course vary depending on the mode of administration, the particular condition to be treated and the effect desired. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 1 to 50 mg active ingredient.

The compounds of Formula I can be administered by any conventional route, in particular enterally, for example, orally, e.g. in the form of tablets or capsules, or parenterally, for example, in the form of injectable solutions or suspensions, topically, e.g. in the form of lotions, gels, ointments or creams, or in a nasal or a suppository form. Pharmaceutical compositions comprising a compound of Formula I in free form or in pharmaceutically acceptable salt form in association with at least one pharmaceutical acceptable carrier or diluent can be manufactured in conventional manner by mixing with a pharmaceutically acceptable carrier or diluent.

The compounds of Formula I can be administered in free form or in pharmaceutically acceptable salt form, for example, as indicated above. Such salts can be prepared in a conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

1.3 A method for inhibiting or controlling deregulated angiogenesis, e.g. sphingosine-1-phosphate (SIP) mediated angiogenesis, in a subject in need thereof, comprising administering to said subject a therapeutically effective amount of a compound of formula I or a pharmaceutically acceptable salt thereof.

1.4 A method for preventing or treating diseases mediated by a neo-angiogenesis process or associated with deregulated angiogenesis in a subject in need thereof, comprising administering to said subject a therapeutically effective amount of a compound of formula I or a pharmaceutically acceptable salt thereof.

2. A compound of formula I, in free form or in a pharmaceutically acceptable salt form for use as a pharmaceutical, e.g. in any of the methods as indicated under 1.1 to 1.4 above.

3. A pharmaceutical composition, e.g. for use in any of the methods as in 1.1 to 1.4 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 to 1.4 above.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g. a malignant cell anti-proliferative agent. For example the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578 or AP23573; an ascomycin having immunosuppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g. monoclonal antibodies to leukocyte receptors, e.g. MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent.

By the term "chemotherapeutic agent" is meant any chemotherapeutic agent and it includes but is not limited to,
 i. an aromatase inhibitor,
 ii. an anti-estrogen, an anti-androgen (especially in the case of prostate cancer) or a gonadorelin agonist,
 iii. a topoisomerase I inhibitor or a topoisomerase II inhibitor,
 iv. a microtubule active agent, an alkylating agent, an antineoplastic antimetabolite or a platin compound,
 v. a compound targeting/decreasing a protein or lipid kinase activity or a protein or lipid phosphatase activity, a further anti-angiogenic compound or a compound which induces cell differentiation processes,
 vi. a bradykinin 1 receptor or an angiotensin II antagonist,
 vii. a cyclooxygenase inhibitor, a bisphosphonate, a histone deacetylase inhibitor, a heparanase inhibitor (prevents heparan sulphate degradation), e.g. PI-88, a biological response modifier, preferably a lymphokine or interferons, e.g. interferon □, an ubiquitination inhibitor, or an inhibitor which blocks anti-apoptotic pathways,
 viii. an inhibitor of Ras oncogenic isoforms, e.g. H-Ras, K-Ras or N-Ras, or a farnesyl transferase inhibitor, e.g. L-744,832 or DK8G557,
 ix. a telomerase inhibitor, e.g. telomestatin,
 x. a protease inhibitor, a matrix metalloproteinase inhibitor, a methionine aminopeptidase inhibitor, e.g. bengamide or a derivative thereof, or a proteosome inhibitor, e.g. PS-341, and/or
 xi. a mTOR inhibitor.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. A combination of the invention comprising a chemotherapeutic agent which is an aromatase inhibitor is particularly useful for the treatment of hormone receptor positive tumors, e.g. breast tumors.

The term "anti-estrogen" as used herein relates to a compound which antagonizes the effect of estrogens at the estrogen receptor level. The term includes, but is not limited to tamoxifen, fulvestrant, raloxifene and raloxifene hydrochloride. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide.

The term "gonadorelin agonist" as used herein includes, but is not limited to abarelix, goserelin and goserelin acetate.

The term "topoisomerase I inhibitor" as used herein includes, but is not limited to topotecan, irinotecan, 9-nitro-camptothecin and the macromolecular camptothecin conjugate PNU-166148 (compound A1 in WO99/17804).

The term "topoisomerase II inhibitor" as used herein includes, but is not limited to the anthracyclines such as doxorubicin, daunorubicin, epirubicin, idarubicin and nemorubicin, the anthraquinones mitoxantrone and losoxantrone, and the podophillotoxines etoposide and teniposide.

The term "microtubule active agent" relates to microtubule stabilizing and microtubule destabilizing agents including, but not limited to taxanes, e.g. paclitaxel and docetaxel, vinca alkaloids, e.g., vinblastine, especially vinblastine sulfate, vincristine especially vincristine sulfate, and vinorelbine, discodermolides and epothilones and derivatives thereof, e.g. epothilone B or a derivative thereof.

The term "alkylating agent" as used herein includes, but is not limited to busulfan, chlorambucil, cyclophosphamide, ifosfamide, melphalan or nitrosourea (BCNU or Gliadel™).

The term "antineoplastic antimetabolite" includes, but is not limited to 5-fluorouracil, capecitabine, gemcitabine, cytarabine, fludarabine, thioguanine, methotrexate and edatrexate.

The term "platin compound" as used herein includes, but is not limited to carboplatin, cis-platin and oxaliplatin.

The term "compounds targeting/decreasing a protein or lipid kinase activity or further anti-angiogenic compounds" as used herein includes, but is not limited to protein tyrosine kinase and/or serine and/or threonine kinase inhibitors or lipid kinase inhibitors, e.g. compounds targeting, decreasing or inhibiting the activity of the epidermal growth factor family of receptor tyrosine kinases (EGFR, ErbB2, ErbB3, ErbB4 as homo- or heterodimers), the vascular endothelial growth factor family of receptor tyrosine kinases (VEGFR), the platelet-derived growth factor-receptors (PDGFR), the fibroblast growth factor-receptors (FGFR), the insulin-like growth factor receptor 1 (IGF-1R), the Trk receptor tyrosine kinase family, the Axl receptor tyrosine kinase family, the Ret receptor tyrosine kinase, the Kit/SCFR receptor tyrosine kinase, members of the c-Abl family and their gene-fusion products (e.g. BCR-Abl), members of the protein kinase C (PKC) and Raf family of serine/threonine kinases, members of the MEK, SRC, JAK, FAK, PDK or PI(3) kinase family, or of the PI(3)-kinase-related kinase family, and/or members of the cyclin-dependent kinase family (CDK) and anti-angiogenic compounds having another mechanism for their activity, e.g. unrelated to protein or lipid kinase inhibition.

Compounds which target, decrease or inhibit the activity of VEGFR are especially compounds, proteins or antibodies which inhibit the VEGF receptor tyrosine kinase, inhibit a VEGF receptor or bind to VEGF, and are in particular those compounds, proteins or monoclonal antibodies generically and specifically disclosed in WO 98/35958, e.g. 1-(4-chloroanilino)-4-(4-pyridylmethyl)phthalazine or a pharmaceutically acceptable salt thereof, e.g. the succinate, in WO 00/27820, e.g. a N-aryl(thio) anthranilic acid amide derivative e.g. 2-[(4-pyridyl)methyl]amino-N-[3-methoxy-5-(trifluoromethyl)phenyl]benzamide or 2-[(1-oxido-4-pyridyl)methyl]amino-N-[3-trifluoromethylphenyl]benzamide, or in WO 00/09495, WO 00/59509, WO 98/11223, WO 00/27819 and EP 0 769 947; those as described by M. Prewett et al in Cancer Research 59 (1999) 5209–5218, by F. Yuan et al in Proc. Natl. Acad. Sci. USA, vol. 93, pp. 14765–14770, December 1996, by Z. Zhu et al in Cancer Res. 58, 1998, 3209–3214, and by J. Mordenti et al in Toxicologic Pathology, Vol. 27, no. 1, pp 14–21, 1999; in WO 00/37502 and WO 94/10202; Angiostatin™, described by M. S. O'Reilly et al, Cell 79, 1994, 315–328; Endostatin™, described by M. S. O'Reilly et al, Cell 88, 1997, 277–285; anthranilic acid amides; ZD4190; ZD6474; SU5416; SU6668; or anti-VEGF antibodies or anti-VEGF receptor antibodies, e.g. RhuMab.

By antibody is meant intact monoclonal antibodies, polyclonal antibodies, multispecific antibodies formed from at least 2 intact antibodies, and antibody fragments so long as they exhibit the desired biological activity.

Compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, or which have a dual inhibiting effect on the ErbB and VEGF receptor kinase and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180) or PCT/EP02/08780; e.g. trastuzumab (Herpetin®), cetuximab, Iressa, OSI-774, CI-1033, EKB-569, GW-2016, E1.1, E2.4, E2.5, E6.2, E6.4, E2.11, E6.3 or E7.6.3.

Compounds which target, decrease or inhibit the activity of PDGFR are especially compounds which inhibit the PDGF receptor, e.g. a N-phenyl-2-pyrimidine-amine derivative, e.g. imatinib.

Compounds which target, decrease or inhibit the activity of c-Abl family members and their gene fusion products are, e.g. a N-phenyl-2-pyrimidine-amine derivative, e.g. imatinib; PD180970; AG957; or NSC 680410.

Compounds which target, decrease or inhibit the activity of protein kinase C, Raf, MEK, SRC, JAK, FAK and PDK family members, or PI(3) kinase or PI(3) kinase-related family members, and/or members of the cyclin-dependent kinase family (CDK) are especially those staurosporine derivatives disclosed in EP 0 296 110, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; or LY333531/LY379196.

Further anti-angiogenic compounds are e.g. thalidomide (THALOMID) and TNP-470.

Compounds which target, decrease or inhibit the activity of a protein or lipid phosphatase are, e.g. inhibitors of phosphatase 1, phosphatase 2A, PTEN or CDC25, e.g. okadaic acid or a derivative thereof.

Compounds which induce cell differentiation processes are, e.g. retinoic acid, α-, γ- or δ-tocopherol or α-, γ- or δ-tocotrienol.

The term cyclooxygenase inhibitor as used herein includes, but is not limited to, e.g. celecoxib (Celebrex®), rofecoxib (Vioxx®), etoricoxib, valdecoxib or a 5-alkyl-2-arylaminophenylacetic acid, e.g. 5-methyl-2-(2'-chloro-6'-fluoroanilino)phenyl acetic acid.

The term "histone deacetylase inhibitor" as used herein includes, but is not limited to MS-27-275, SAHA, pyroxamide, FR-901228 or valproic acid.

The term "bisphosphonates" as used herein includes, but is not limited to, etridonic, clodronic, tiludronic, pamidronic, alendronic, ibandronic, risedronic and zoledronic acid.

The term "matrix metalloproteinase inhibitor" as used herein includes, but is not limited to collagen peptidomimetic and non-petidomimetic inhibitors, tetracycline derivatives, e.g. hydroxamate peptidomimetic inhibitor batimastat and its orally bioavailable analogue marimastat, prinomastat, BMS-279251, BAY 12-9566, TAA211 or AAJ996.

The term "mTOR inhibitor" as used herein includes, but is not limited to rapamycin (sirolimus) or a derivative thereof, e.g. 32-deoxorapamycin, 16-pent-2-ynyloxy-32-deoxorapamycin, 16-pent-2-ynyloxy-32(S)-dihydro-rapamycin, 16-pent-2-ynyloxy-32(S)-dihydro-40-O-(2-hydroxyethyl)-rapamycin and, more preferably, 40-O-(2-hydroxyethyl)-rapamycin. Further examples of rapamycin derivatives include e.g. CCI779 or 40-[3-hydroxy-2-(hydroxymethyl)-2-methylpropanoate]-rapamycin or a pharmaceutically acceptable salt thereof, as disclosed in U.S. Pat. No. 5,362,718, ABT578 or 40-(tetrazolyl)-rapamycin, particularly 40-epi-(tetrazolyl)-rapamycin, e.g. as disclosed in WO 99/15530, or rapalogs as disclosed e.g. in WO 98/02441 and WO01/14387, e.g. AP23573.

Where the compounds of formula I are administered in conjunction with other immunosuppressive/immunomodulatory, anti-inflammatory or chemotherapeutic therapy, dosages of the co-administered immunosuppressant, immunomodulatory, anti-inflammatory or chemotherapeutic compound will of course vary depending on the type of co-drug employed, e.g. whether it is a steroid or a calcineurin inhibitor, on the specific drug employed, on the condition being treated and so forth.

In accordance with the foregoing the present invention provides in a yet further aspect:

5. A method as defined above comprising co-administration, e.g. concomitantly or in sequence, of a therapeutically effective non-toxic amount of a compound of formula I and at least a second drug substance, e.g. an immunosuppressant, immunomodulatory, anti-inflammatory or chemotherapeutic drug, e.g. as indicated above.

6. A pharmaceutical combination, e.g. a kit, comprising a) a first agent which is a compound of formula I as disclosed herein, in free form or in pharmaceutically acceptable salt form, and b) at least one co-agent, e.g. an immunosuppressant, immunomodulatory, anti-inflammatory or chemotherapeutic drug, e.g. as disclosed above. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Methods for Preparing Compounds of the Invention

The present invention also includes processes for the preparation of immunomodulatory compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, wherein $R^1$ is a group of formula (a), can be prepared by proceeding as in the following Reaction scheme 1:

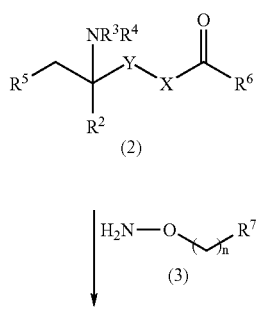

(2)

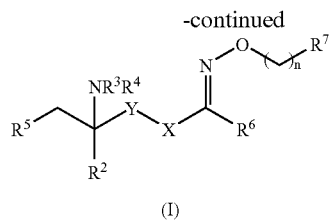

(I)

in which n, $R^2$, $R^3$, $R^4$, $R^5$, $R^6$, $R^7$, X and Y are as defined for Formula I above.

Compounds of Formula I can be prepared by reacting a compound of Formula 2 with a compound of Formula 3. The reaction can be effected in a suitable acid (e.g., acetic acid, or the like) and can take 1 to 20 hours to complete.

Compounds of Formula I can be prepared by removing the hydrolysable groups present in a compound of Formula 4:

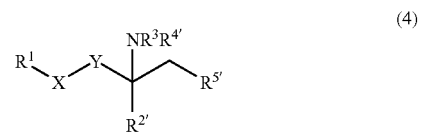

wherein X, Y, $R^1$ and $R^3$ are as defined above, $R^{4'}$ is an amino protecting group, $R^{2'}$ has one of the significances given for $R^2$ above except that the terminal OH when present in the OH-substituted $C_{1-4}$alkyl is in protected form or the residue of formula (g) is replaced by a residue of formula (g') and $R^{5'}$ is $R^{5'''}$ in which $R^{5'''}$ is H, —OH in protected form or a residue of formula (g'), provided that at least one of $R^{2'}$ and $R^{5'}$ is OH in protected form or a residue of formula (g'), the residue of formula (g') being:

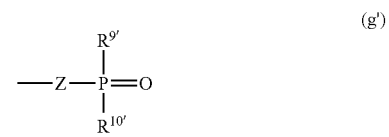

wherein each of $R^{9'}$ and $R^{10'}$ is a hydrolysable group and, where required, converting the compounds of Formula I obtained in free form into the desired salt form, or vice versa.

The process can be carried out in accordance with methods known in the art. Hydrolysable groups can be hydroxy and amino protecting groups, for example, when compounds of Formula I are free of a residue of formula (g), and/or groups such as $R^{9'}$ and $R^{10'}$. Examples of protecting groups for hydroxy and amino groups are, for example, as disclosed in "Protective Groups in Organic Synthesis" T. W. Greene, J. Wiley & Sons N.Y., 2$^{nd}$ ed., chapter 7, 1991, and references therein, for example benzyl, p-methoxybenzyl, methoxymethyl, tetrahydropyranyl, trialkylsilyl, acyl, tert-butoxy-carbonyl, benzyloxy-carbonyl, 9-fluorenylmethoxycarbonyl, trifluoroacetyl, trimethylsilylethanesulfonyl and the like.

Preferably $R^{9'}$ and $R^{10'}$ are identical and have the significance of, for example, phenoxy or benzoxy or form together a cyclic system such as in 1,5-dihydro-2,4,3-benzodioxaphosphepin.

The removal of the hydroxy and amino protecting groups and/or of $R^{4'}$ or $R^{6'}$ groups in the compounds of formula 4 can conveniently be performed according to methods known in the art, for example, by hydrolysis, for example, in a basic medium, for example using a hydroxide such as barium hydroxide. It can also be performed by hydrogenolysis, for example, in the presence of Pearlman's catalyst, for example, as disclosed in J. Org. Chem., 1998, 63, 2375–2377. When the compounds of formula 4 are free of a residue of formula (g'), the removal of the hydroxy and amino protecting groups can also be performed in an acidic medium.

Additional Processes for Preparing Compounds of the Invention:

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferable, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from the their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) reacting a compound of Formula (2) with a compound of Formula (3):

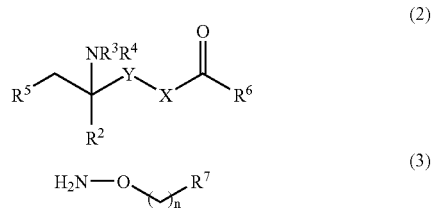

in which n, $R^2$, $R^3$, $R^4$, $R^5$, $R^6$, $R^7$, X and Y are as defined for Formula I above; or (b) removing the hydrolysable groups present in a compound of Formula 4:

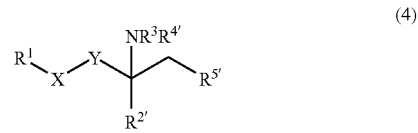

in which $R^1$, $R^{2'}$, $R^3$, $R^{4'}$, $R^{5'}$, X and Y are as defined for Formula I above; or (c) optionally converting a compound of the invention into a pharmaceutically acceptable salt;

(d) optionally converting a salt form of a compound of the invention to a non-salt form;

(e) optionally converting an unoxidized form of a compound of the invention into a pharmaceutically acceptable N-oxide;

(f) optionally converting an N-oxide form of a compound of the invention to its unoxidized form;

(g) optionally resolving an individual isomer of a compound of the invention from a mixture of isomers;

(h) optionally converting a non-derivatized compound of the invention into a pharmaceutically acceptable prodrug derivative; and (i) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following examples provide detailed descriptions of the preparation of representative compounds and are offered to illustrate, but not to limit the present invention.

Example 1

1-[4-(3-Amino-4-hydroxy-3-hydroxymethyl-butyl)-phenyl]-ethanone-O-biphenyl-4-ylmethyl-oxime

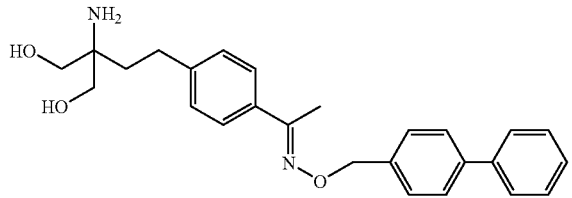

Step A: 2-Acetylamino-2-(2-oxo-2-phenyl-ethyl)-malonic acid diethyl ester

Sodium hydride (15 mmol) is added to anhydrous ethanol (50 mL) and to the resulting sodium ethoxide solution is added 2-acetylaminomalonic acid diethyl ester (15 mmol) in one portion. The resulting mixture is stirred at room temperature for 30 minutes. A solution of 2-bromoacetophenone (10 mmol) in ethanol (10 mL) is then added and the resulting mixture is stirred at room temperature for 12 hours. After concentrating under reduced pressure, the residue is dissolved in EtOAc and water. The organic phase is washed with brine and dried over $Na_2SO_4$. After removal of the solvent, the crude material is purified by column chromatography using EtOAc/hexane (1/3) giving 2-acetylamino-2-(2-oxo-2-phenyl-ethyl)-malonic acid diethyl ester as white solid; MS: (ES$^+$): 336.1 (M+1)$^+$.

Step B: Acetic acid 4-acetoxy-2-acetoxymethyl-2-acetylamino-4-phenyl-butyl ester To a solution of 2-acetylamino-2-(2-oxo-2-phenyl-ethyl)-malonic acid diethyl ester (5 mmol) in 95% EtOH (50 mL) is added $NaBH_4$ (25 mmol) in portions. After stirring at room temperature for 3 hours, the reaction is quenched with saturated $NH_4Cl$. After removal of EtOH under reduced pressure, the aqueous solution is extracted with EtOAc. The organic phase is washed with brine and dried over $Na_2SO_4$. After concentrating, the residue is dissolved in anhydrous $CH_2Cl_2$ (25 mL). $Ac_2O$ (30 mmol) and pyridine (60 mmol) are then added. After stirring at room temperature for 12 hours, it is sequentially washed with 1 N HCl, saturated $NaHCO_3$, and brine and dried over $Na_2SO_4$. After removal of the solvent, the crude material is purified by column chromatography using EtOAc/hexane (1/1) to give acetic acid 4-acetoxy-2-acetoxymethyl-2-acetylamino-4-phenyl-butyl ester as a white solid; MS: (ES$^+$): 380.2 (M+1)$^+$.

Step C: Acetic acid 2-acetoxymethyl-2-acetylamino-4-phenyl-butyl ester

Acetic acid 2-acetoxymethyl-2-acetylamino-4-phenyl-butyl ester (5 mmol) is dissolved in EtOH (50 mL) and hydrogenated at atmospheric pressure using 10% Pd—C (10%) at room temperature for 12 hours. After filtration and concentration, the crude product is obtained as a white solid and used in the next step without further purification; MS: (ES$^+$): 322.2 (M+1)$^+$.

Step D: Acetic acid 2-acetoxymethyl-2-acetylamino-4-(4-acetyl-phenyl)-butyl ester To a suspension of $AlCl_3$ (16 mmol) in DCE (20 mL) is added AcCl (8 mmol) in one portion. After stirring at room temperature for 30 minutes, to the solution is added acetic acid 2-acetoxymethyl-2-acetylamino-4-phenyl-butyl ester (2 mmol) in DCE (5 mL). After an additional 30 minutes, the mixture is poured into ice-cold 1 N NaOH and is extracted with DCM. The organic phase is washed with 1 N HCl, brine and dried over $Na_2SO_4$. After concentrating, the crude material is purified by column chromatography using EtOAc/hexane (2/1) to give acetic acid 2-acetoxymethyl-2-acetylamino-4-(4-acetyl-phenyl)-butyl ester as a white solid. MS: (ES$^+$): 364.2 (M+1)$^+$.

Step E: 1-[4-(3-Amino-4-hydroxy-3-hydroxymethyl-butyl)-phenyl]-ethanone O-biphenyl-4-ylmethyl-oxime To a solution of acetic acid 2-acetoxymethyl-2-acetylamino-4-(4-acetyl-phenyl)-butyl ester (0.2 mmol) in MeOH (1 mL) is added O-(4-phenyl)benzyloxyamine hydrochloride salt (0.24 mmol) and $Et_3N$ (0.23 mmol). After stirring at room temperature for 12 hours, it is concentrated and the residue is dissolved in DCM, which is washed with brine and dried over $Na_2SO_4$. After concentrating, the crude product is dissolved in THF (1 mL) and treated with 2 N LiOH aqueous solution (0.5 mL). The resulting mixture is stirred at reflux for 1 hour and diluted with $H_2O$ (10 mL). It is then extracted with EtOAc (3×5 mL) and the combined organic phase is washed with brine and dried over $Na_2SO_4$. After concentrating, the crude product is purified with LC-MS to give 1-[4-(3-amino-4-hydroxy-3-hydroxymethyl-butyl)-phenyl]-ethanone O-biphenyl-4-ylmethyl-oxime as a white solid; MS: (ES$^+$): 419.2 (M+1)$^+$.

Example 2

Phosphoric acid mono-(2-amino-4-{4-[1-(4'-fluoro-biphenyl-4-ylmethoxyimino)-ethyl]-phenyl}-2-hydroxymethyl-butyl)ester

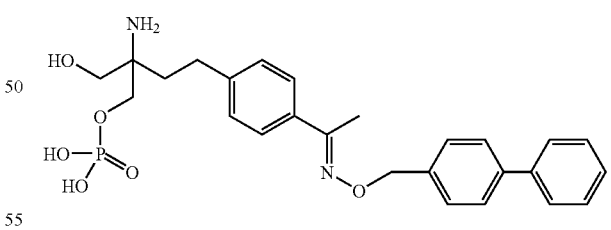

Step A: 1-{4-[2-(4-Hydroxymethyl-2-methyl-4,5-dihydro-oxazol-4-yl)-ethyl]-phenyl}-ethanone To a suspension of 1-[4-(3-amino-4-hydroxy-3-hydroxymethyl-butyl)-phenyl]-ethanone (1 mmol) in anhydrous dichloroethane (2 mL) is added triethylorthoacetate (1.1 mmol) and acetic acid (0.05 mmol). The resulting mixture is heated at 80° C. for 12 hours. After concentration, the residue is purified by flash column chromatography (EtOAc) to give 1-{4-[2-(4-hydroxymethyl-2-methyl-4,5-dihydro-oxazol-4-yl)-ethyl]-phenyl}-ethanone as an oil; MS: (ES$^+$): 262.1 (M+1)$^+$.

Step B: Phosphoric acid 4-[2-(4-acetyl-phenyl)-ethyl]-2-methyl-4,5-dihydro-oxazol-4-ylmethyl ester di-tert-butyl ester To a solution of 1-{4-[2-(4-hydroxymethyl-2-methyl-4,5-dihydro-oxazol-4-yl)-ethyl]-phenyl}-ethanone (1 mmol) in dry tetrahydrofuran (5 mL) is added 1H-tetrazole (6 mmol) and di-tert-butyl diisopropylphosphorimidite (3 mmol). The resulting mixture is stirred at room temperature for 4 hours. A solution of mCPBA (3 mmol) in dichloromethane (5 mL) is then added. After an additional 1 hour, the reaction mixture is diluted with water (20 mL) and dichloromethane (10 mL). The aqueous layer is extracted with dichloromethane (10 mL). The combined organic layer is washed with brine and dried over anhydrous $Na_2SO_4$. After concentration, the residue is purified by flash column chromatography (30% EtOAc/hexane) to give phosphoric acid 4-[2-(4-acetyl-phenyl)-ethyl]-2-methyl-4,5-dihydro-oxazol-4-ylmethyl ester di-tert-butyl ester as an oil; MS: ($ES^+$): 454.2 $(M+1)^+$.

Step C: Phosphoric acid mono-(2-amino-4-{4-[1-(biphenyl-4-ylmethoxyimino)-ethyl]-phenyl}-2-hydroxymethyl-butyl) ester A solution of phosphoric acid 4-[2-(4-acetyl-phenyl)-ethyl]-2-methyl-4,5-dihydro-oxazol-4-ylmethyl ester di-tert-butyl ester (0.2 mmol) in 5% aqueous HCl (1 mL) and THF (2 mL) is heated at reflux for 2 hours. After concentration, methanol (2 mL) is added to the residue followed by the addition of O-(4-phenyl)benzyloxyamine (0.3 mmol). The solution is then neutralized by $Na_2CO_3$ to pH 6. The resulting mixture is then stirred at room temperature for 12 hours. After concentration, the residue is purified by preparative LCMS to give phosphoric acid mono-(2-amino-4-{4-[1-(biphenyl-4-ylmethoxyimino)-ethyl]-phenyl}-2-hydroxymethyl-butyl)ester as a white solid; MS: ($ES^+$): 499.2 $(M+1)^+$.

By repeating the procedure described in the above examples, using appropriate starting materials, the following compounds of Formula I are obtained as identified in Table 1.

TABLE 1

| Compound No. | n | $R^2$ | $R^7$ | Physical Data MS (M + 1) |
|---|---|---|---|---|
| 3 | 1 | —OP(O)(OH)$_2$ | biphenyl with 2-CF$_3$ | 567.2 |
| 4 | 1 | —OP(O)(OH)$_2$ | biphenyl with 4-CF$_3$ | 567.2 |
| 5 | 1 | —OP(O)(OH)$_2$ | biphenyl with 3-CF$_3$ | 567.2 |
| 6 | 1 | —OP(O)(OH)$_2$ | biphenyl with 3-OCF$_3$ | 583.15 |
| 7 | 1 | —OP(O)(OH)$_2$ | biphenyl with 4-OCF$_3$ | 583.2 |

TABLE 1-continued
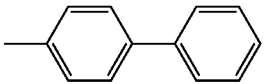
| Compound No. | n | R² | R⁷ | Physical Data MS (M + 1) |
|---|---|---|---|---|
| 8 | 0 | —OP(O)(OH)₂ | 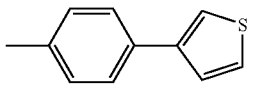 | 485.2 |
| 9 | 1 | —OP(O)(OH)₂ | 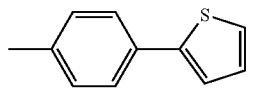 | 505.1 |
| 10 | 1 | —OP(O)(OH)₂ | 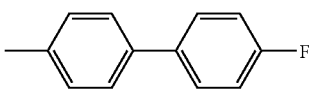 | 505.1 |
| 11 | 1 | —OP(O)(OH)₂ | 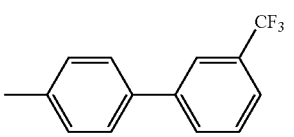 | 517.2 |
| 12 | 1 | —OH | 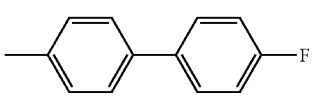 | 487.2 |
| 13 | 1 | —OH | 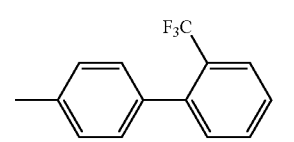 | 437.2 |
| 14 | 1 | —OH | 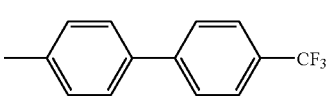 | 487.2 |
| 15 | 1 | —OH | 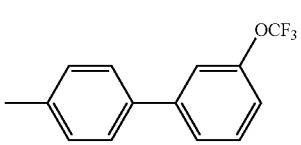 | 487.2 |
| 16 | 1 | —OH | 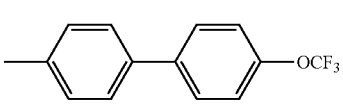 | 503.2 |
| 17 | 1 | —OH | 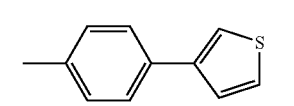 | 503.2 |
| 18 | 1 | —OH |  | 425.2 |

TABLE 1-continued

| Compound No. | n | R² | R⁷ | Physical Data MS (M + 1) |
|---|---|---|---|---|
| 19 | 1 | —OH | 4-(thiophen-2-yl)phenyl | 425.2 |
| 20 | 0 | —OH | biphenyl-4-yl | 405.2 |
| 21 | 2 | —OH | biphenyl-4-yl | 433.2 |
| 22 | 1 | —OH | 4-(furan-3-yl)phenyl | 409.2 |
| 23 | 1 | —OH | 2'-methoxybiphenyl-4-yl | 449.2 |
| 24 | 1 | —OH | 3'-methoxybiphenyl-4-yl | 449.2 |
| 25 | 1 | —OH | 4'-methoxybiphenyl-4-yl | 449.2 |
| 26 | 1 | —OH | 4-cyclohexylphenyl | 425.3 |
| 27 | 1 | —OH | 3-fluoro-biphenyl-4-yl | 437.2 |
| 28 | 1 | —OH | 5-phenylthiophen-2-yl | 425.2 |

TABLE 1-continued
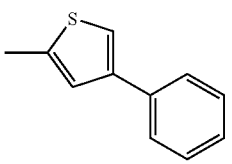
| Compound No. | n | R² | R⁷ | Physical Data MS (M + 1) |
|---|---|---|---|---|
| 29 | 1 | —OH | 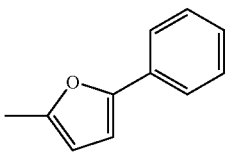 | 425.2 |
| 30 | 1 | —OH | 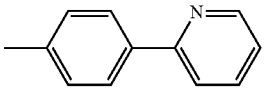 | 409.2 |
| 31 | 1 | —OH | 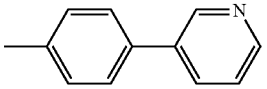 | 420.2 |
| 32 | 1 | —OH | 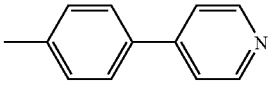 | 420.2 |
| 33 | 1 | —OH | 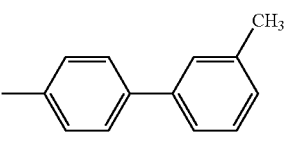 | 420.2 |
| 34 | 1 | —OH | 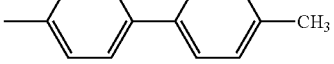 | 433.2 |
| 35 | 1 | —OH | 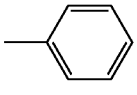 | 433.2 |
| 36 | 3 | —OH | 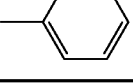 | |
| 37 | 5 | H | | |

Example 3

Compounds of Formula I Exhibit Biological Activity

A. In vitro: a Scintillation Proximity Assay (SPA) for Measuring GTP [γ-$^{35}$S] Binding to Membranes Prepared from CHO Cells Expressing Human EDG/S1P Receptors EDG-1 (S1P1) GTP [γ-$^{35}$S] binding assay: Membrane protein suspensions are prepared from CHO cell clones stably expressing a human EDG-1 N-terminal c-myc tag. Solutions of test compounds ranging from 10 mM to 0.01 mM are prepared in DMSO/50 mM HCl and then diluted into assay buffer (20 mM HEPES, pH7.4, 100 mM NaCl, 10 mM MgCl2, 0.1% fat free BSA). Assay buffer containing 10 mM GDP is mixed with wheat germ agglutinin-coated SPA-beads (1 mg/well) followed by the addition of human EDG-1 membrane protein suspension (10 µg/well) and test compound. The bead/membrane/compound assay components are then mixed for 10–15 minutes on a shaker at room temperature. GTP [γ-$^{35}$S] (200 pM) and bead/membrane/compound assay mixture are added to individual wells of a 96 well Optiplate™ (final volume 225 µl/well), sealed and incubated at room temperature for 110 to 120 minutes under constant shaking. After centrifugation (2000 rpm, 10 minutes) luminescence is measured with a TopCount™ instrument.

EC50 values are obtained by fitting the GTP [γ-$^{35}$S] binding curves (raw data) with the dose response curve-fitting tool of ORIGIN V. 6.1. Basal binding (no compound) and the highest stimulation of GTP [γ-$^{35}$S] binding achieved by an agonist are used as the fitting range. Seven different concentrations are used to generate a concentration response curve (using two or three data points per concentration).

EDG-3,-5,-6 and -8 GTP [γ-$^{35}$S] binding assays are carried out in a comparable manner to the EDG-1 GTP [[γ-$^{35}$S] binding assay using membranes from CHO, or in the case of EDG-8 RH7777 membranes, from cells stably expressing c-terminal c-myc tagged or untagged receptors. Concentrations of EDG receptor expressing membranes range between 13–19 µg per well. Compounds of the invention were tested according to the above assay and were observed to exhibit selectivity for the EDG-1 receptor (table 2). For example, phosphoric acid mono-(2-amino-2-hydroxymethyl-4-{4-[1-(4-thiophen-2-yl-benzyloxy-imino)-ethyl]-phenyl}-butyl) ester (Compound 10 & Table 2) has an EC$_{50}$ of 1.15 nM in the above assay and is at least 1000 fold selective for EDG-1 compared to EDG-3, EDG-5, EDG-6 and EDG-8.

TABLE 2

Activities of Some EDG-1 Selective Compounds

| Compound | Lymphocyte Depletion ED50 (mg/kg) | Heart effect in conscious mice | EDG-1 EC50 (nM) | EDG-3 EC50 (nM) | EDG-5 EC50 (nM) | EDG-6 EC50 (nM) | EDG-8 EC50 (nM) |
|---|---|---|---|---|---|---|---|
| 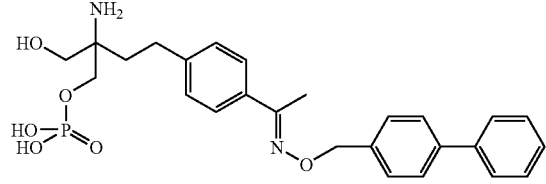 | ED50 ~0.1 | clean | 0.86 | >10000 | >10000 | 168 | >10000 |
| 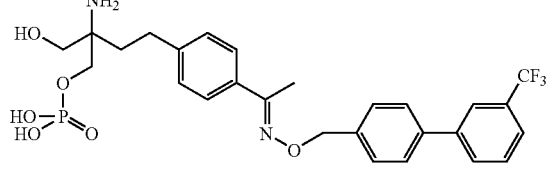 | ED50 <1 | clean | 15.71 | 3.5 | >10000 | 1244.5 | 5.8 |
| 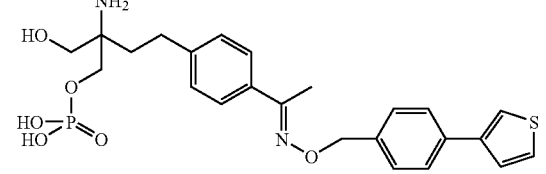 | ED50 ~0.08 | clean | 0.79 | >10000 | >10000 | 4400.0 | >10000 |
| 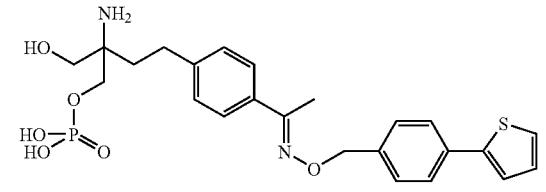 | ED50 ~0.2 | clean | 1.15 | >10000 | >10000 | >10000 | >10000 |

B. In Vitro: FLIPR Calcium Flux Assay

Compounds of the invention are tested for agonist activity on EDG-1, EDG-3, EDG-5, and EDG-6 with a FLIPR calcium flux assay. Briefly, CHO cells expressing an EDG receptor are maintained in F-12K medium (ATCC), containing 5% FBS, with 500 ug/ml of G418. Prior to the assay, the cells are plated in 384 black clear bottom plates at the density of 10,000 cells/well/25 µl in the medium of F-12K containing 1% FBS. The second day, the cells are washed three times (25 µl/each) with washing buffer. About 25 µl of dye are added to each well and incubated for 1 hour at 37° C. and 5% $CO_2$. The cells are then washed four times with washing buffer (25 µl/each). The calcium flux is assayed after adding 25 µl of SEQ2871 solution to each well of cells. The same assay is performed with cells expressing each of the different EDG receptors. Titration in the FLIPR calcium flux assay is recorded over a 3-minute interval, and quantitated as maximal peak height percentage response relative to EDG-1 activation.

C. In Vivo: Screening Assays for Measurement of Blood Lymphocyte Depletion and Assessment of Heart Effect Measurement of circulating lymphocytes: Compounds are dissolved in DMSO and further diluted with deionized water. Mice (C57bl/6 male, 6–10 week-old) are administered 20 µg of compound (diluted in 200 µl water, 4% DMSO) via intra-peritoneal (IP) injection under short isoflurane anesthesia. Water (200 µl), 4% DMSO, and FTY720 (10 µg) are included as negative and positive controls, respectively.

Blood is collected from the retro-orbital sinus 18 hours after drug administration under short isoflurane anesthesia. Whole blood samples are subjected to hematology analysis. Peripheral lymphocyte counts are determined using an automated analyzer. Subpopulations of peripheral blood lymphocytes are stained by fluorochrome-conjugated specific antibodies and analyzed using a fluorescent activating cell sorter (Facscalibur). Two mice are used to assess the lymphocyte depletion activity of each compound screened. The result is an $ED_{50}$, which is defined as the effective dose required displaying 50% of blood lymphocyte depletion. Compounds of the invention were tested according to the above assay and were preferably found to exhibit an $ED_{50}$ of less than 1 mg/kg, more preferably an $ED_{50}$ of less than 0.5 mg/kg. For example, compound 9 exhibits an ED50 of 0.08 mg/kg.

Assessment of Heart Effect: The effects of compounds on cardiac function are monitored using the AnonyMOUSE ECG screening system. Electrocardiograms are recorded in conscious mice (C57bl/6 male, 6–10 week-old) before and after compound administration. ECG signals are then processed and analyzed using the e-MOUSE software. 90 µg of compound further diluted in 200 µl water, 15% DMSO are injected IP. Four mice are used to assess the heart effect of each compound.

D: In Vivo: Anti-Angiogenic Activity

Porous chambers containing (i) sphingosine-1-phosphate (5 µM/chamber) or (ii) human VEGF (1 µg/chamber) in 0.5 ml of 0.8% w/v agar (containing heparin, 20 U/ml) are implanted subcutaneously in the flank of mice. S1P or VEGF induces the growth of vascularized tissue around the chamber. This response is dose-dependent and can be quantified by measuring the weight and blood content of the tissue. Mice are treated once a day orally or intravenously with a compound of formula I starting 4–6 hours before implantation of the chambers and continuing for 4 days. The animals are sacrificed for measurement of the vascularized tissues 24 hours after the last dose. The weight and blood content of the vascularized tissues around the chamber is determined. Animals treated with a compound of formula I show reduced weight and/or blood content of the vascularized tissues compared to animals treated with vehicle alone. Compounds of Formula I are anti-angiogenic when administered at a dose of about 0.3 to about 3 mg/kg.

E: In Vitro: Antitumor Activity

A mouse breast cancer cell line originally isolated from mammary carcinomas is used, e.g. JygMC(A). The cell number is adjusted to $5 \times 10^5$ for plating in fresh medium before the procedure. Cells are incubated with fresh medium containing 2.5 mM of thymidine without FCS for 12 hours and then washed twice with PBS, followed by addition of fresh medium with 10% FCS and additionally incubated for another 12 hours. Thereafter the cells are incubated with fresh medium containing 2.5 mM of thymidine without FCS for 12 hours. To release the cells from the block, the cells are washed twice with PBS and replated in fresh medium with 10% FCS. After synchronization, the cells are incubated with or without various concentrations of a compound of formula I for 3, 6, 9, 12, 18 or 24 hours. The cells are harvested after treatment with 0.2% EDTA, fixed with ice-cold 70% ethanol solution, hydrolyzed with 250 □g/ml of RNaseA (type 1-A: Sigma Chem. Co.) at 37° C. for 30 minutes and stained with propidium iodide at 10 mg/ml for 20 minutes. After the incubation period, the number of cells is determined both by counting cells in a Coulter counter and by the SRB calorimetric assay. Under these conditions compounds of formula I inhibit the proliferation of the tumor cells at concentrations ranging from $10^{-12}$ to $10^{-6}$ M.

It is understood that the examples and embodiments described herein are for illustrative purposes only and that various modifications or changes in light thereof will be suggested to persons skilled in the art and are to be included within the spirit and understanding of this application and scope of the appended claims. All publications, patents, and patent applications cited herein are hereby incorporated by reference for all purposes.

We claim:

1. A compound of Formula I:

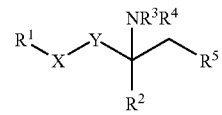

wherein:

Y is —$CH_2CH_2$—, —$CH_2CH(OH)$—, —$CH(OH)CH_2$—, —$C(O)CH_2$—, —$CH_2C(O)$—, —CH=CH— or 1,2-cyclopropylene;

X is arylene or $C_{5-6}$heteroarylene optionally substituted by one to three substituents selected from halo, $C_{1-10}$alkyl and halo-substituted $C_{1-6}$alkyl;

$R^1$ is a group of formula (a), (b), (c), (d), (e) or (f):

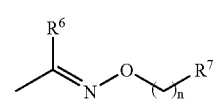

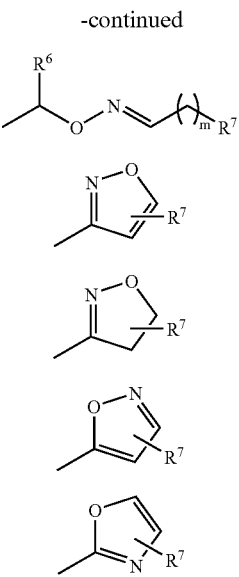

in which n is 0, 1, 2, 3, 4 or 5; m is 0, 1 or 2;

$R^6$ is $C_{1-10}$alkyl, cycloalkyl, $C_{1-10}$alkoxy, $C_{2-10}$alkenyl, $C_{2-10}$alkynyl, $C_{1-10}$alkylthio, $C_{1-10}$alkylsulfonyl, $C_{1-10}$alkylsulfinyl or halo-substituted-$C_{1-10}$alkyl; in each of which any aliphatic part of the group can be straight chain or branched and can be optionally substituted by up to three hydroxy, cycloalkyl, or $C_{1-4}$alkoxy groups and optionally interrupted by a double or triple bond or one or more C(O), $NR^{12}$, S, S(O), S(O)$_2$ or O groups, $R^7$ is aryl or $C_{5-6}$heteroaryl optionally substituted by aryl, $C_{5-6}$heteroaryl or $C_{3-8}$heterocycloalkyl wherein any aryl, heteroaryl or heterocycloalkyl group of $R^7$ can be optionally substituted by one to three substituents selected from halogen, $C_{1-10}$alkyl, $C_{1-10}$alkoxy, halo-substituted-$C_{1-10}$alkyl and halo-substituted-$C_{1-10}$alkoxy;

$R^2$ is hydrogen; $C_{1-4}$alkyl optionally substituted with one or more halogens; $C_{2-6}$ alkenyl, $C_{2-6}$alkynyl, or cycloalkyl optionally substituted by halogen; or $C_{1-4}$alkyl optionally substituted on the terminal C atom by OH or a residue of formula (g):

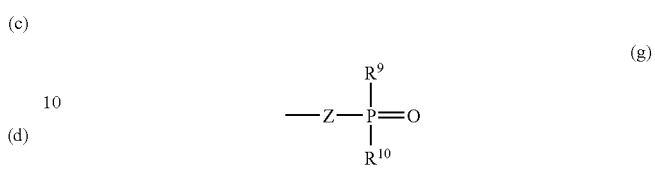

in which Z is O, S, (CH$_2$)$_{1-2}$, CF$_2$ or NR$^{11}$ where R$^{11}$ is H, (C$_{1-4}$)alkyl or halo substituted (C$_{1-4}$)alkyl; and R$^9$ and R$^{10}$, independently, are H, OH, (C$_{1-4}$)alkyl optionally substituted by one to three halo groups, or (C$_{1-4}$)alkoxy; with the proviso that R$^9$ and R$^{10}$ are not both hydrogen;

R$^3$ and R$^4$, independently, are H or C$_{1-4}$alkyl optionally substituted by halogen or acyl; and R$^5$ is —OH, —Oacyl, —NHacyl, or a residue of formula (g) as defined above; or a salt thereof.

2. A compound of claim 1 wherein Y is —CH$_2$—CH$_2$— or —CH(OH)—CH$_2$—.

3. A compound of claim 1 in which X is thiophenylene or phenylene.

4. A compound of claim 1 in which R$^1$ is a group of formula (a); R$^6$ is C$_{1-6}$alkyl, R$^7$ is thiophenyl, furanyl, pyridinyl or phenyl optionally substituted by thiophenyl, furanyl, pyridinyl, phenyl or cyclohexyl wherein any thiophenyl, furanyl, pyridinyl, phenyl or cyclohexyl of R$^7$ can be optionally substituted by one to three substituents selected from halogen, halo-substituted-C$_{1-10}$alkyl and halo-substituted-C$_{1-10}$alkoxy.

5. A pharmaceutical composition comprising a therapeutically effective amount of a compound of claim 1 in combination with a pharmaceutically acceptable excipient.

* * * * *